United States Patent [19]

Sallberg et al.

[11] Patent Number: 5,716,779
[45] Date of Patent: Feb. 10, 1998

[54] DIAGNOSTIC ANTIGEN AND A METHOD OF IN VITRO DIAGNOSING AN ACTIVE INFECTION CAUSED BY HEPATITIS C VIRUS

[75] Inventors: Matti Sallberg, Alvsjo; Jerzy Trojnar, Vintrie, both of Sweden

[73] Assignee: Euro-Diagnostic AB, Malmo, Sweden

[21] Appl. No.: 663,260

[22] PCT Filed: Dec. 8, 1994

[86] PCT No.: PCT/SE94/01183

§ 371 Date: Aug. 26, 1996

§ 102(e) Date: Aug. 26, 1996

[87] PCT Pub. No.: WO95/18382

PCT Pub. Date: Jul. 6, 1995

[30] Foreign Application Priority Data

Dec. 27, 1993 [SE] Sweden ................... 9304291

[51] Int. Cl.$^6$ .................. C12Q 1/70; C07K 7/00; C07K 17/00
[52] U.S. Cl. .................. 435/5; 530/325
[58] Field of Search .................. 435/5; 530/325

[56] References Cited

U.S. PATENT DOCUMENTS 4,816,561  3/1989  Todaro ................... 530/324
5,106,726  4/1992  Wang ................... 435/5

OTHER PUBLICATIONS

Sallberg, et al., "Immune response to a single peptide containing an immunodominant region of hepatitis C virus C virus core protein: the isotypes and the recognition site", Immunology Letters, 33:27–34, 1992.

Takamizawa, et al., "Structure and Organization of the hepatitis C virus genome isolated from human carriers", Journal of Virology, 65:1105–1113, Mar. 1991.

Van Regenmortel, "The concept and operational definition of protein epitopes", Phil. Trans. R. Soc. Lond. B 323, 451–466, Jun. 12, 1989.

*Primary Examiner*—Michael P. Woodward
*Assistant Examiner*—Brenda Glass Brunback
*Attorney, Agent, or Firm*—Oblon, Spivak, McClelland, Maier & Neustadt, P.C.

[57] ABSTRACT

A peptide of the formula (SEQ ID NO:1) Met Ser Thr Ash Pro Lys Pro Cys Arg Lys Thr Lys Arg Asn Thr Asn Arg Arg Pro Cys Asp Val Lys Phe Pro Gly Gly, Gly wherein there is a disulfide bridge between the two cysteine residues, is described. Further, a diagnostic antigen in carrier-bound form comprising said peptide is disclosed. Said peptide may be used in a method of in vitro diagnosing an active infection caused by hepatitis C virus.

3 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 28 amino acids
      ( B ) TYPE: amino acid
      ( C ) STRANDEDNESS: single
      ( D ) TOPOLOGY: both ( i i ) MOLECULE TYPE: peptide ( i x ) FEATURE:
      ( A ) NAME/KEY: Binding-site
      ( B ) LOCATION: 8..20
      ( D ) OTHER INFORMATION: /note="DISULFIDE BRIDGE BETWEEN CYS IN POSITION 8 AND CYS IN POSITION 20"

( x i ) SEQUENCE DESCRIPTION: SEQ ID NO:1:

```
Met Ser Thr Asn Pro Lys Pro Cys Arg Lys Thr Lys Arg Asn Thr Asn
 1               5                  10                   15
Arg Arg Pro Cys Asp Val Lys Phe Pro Gly Gly Gly
            20                  25
```

DIAGNOSTIC ANTIGEN AND A METHOD OF IN VITRO DIAGNOSING AN ACTIVE INFECTION CAUSED BY HEPATITIS C VIRUS

This application is the national stage of International Application no. PCT/SE94/01183, filed Dec. 8, 1994.

The present invention relates to a new peptide, to a new diagnostic antigen comprising said peptide and a method of in vitro diagnosing an active infection caused by hepatitis C virus (HCV) which makes use of a diagnostic antigen according to the invention.

BACKGROUND

The hepatitis C virus is one of the most recently identified human pathogenic viruses, first described in 1989 (Choo Q-L, et al., Science 244:359–362 (1989); Kuo G. et al., Science 244:362–364 (1989)). HCV is one of the first of the viruses termed non-A, non-B viruses to be identified. HCV seems to have been the major cause for post transfusional hepatitis since the introduction of HBV screening at blood banks (Kuo, et al., ibid). The world wide spread of HCV has been shown to be similar to that of HBV. Several routs for parenteral infections have been shown, such as needlestick injuries, intravenous drug use, and through immune globulin preparations (Cariani E, et al., Lancet 337:850 (1991); Chamot E, Aquired Immuno Deficiency Syndrome 6:430–431 (1992); Horst H. A., N Engl J Med 325:132–3 (1991)).

HCV has a size of 30–38 nm and is a member of the flaviviridae with a RNA coded genome of approximately 9.5 kilo bases. Based on the homology, the HCV genome has been proposed to code for two or three structural proteins, core and envelope, and perhaps also a matrix protein (Takamizawa A, et al., Journal of Virology 65:1105–13 (1991)).

The structure of the HCV is yet unknown, it can only be assumed by the proposed homology with the other members of the flaviviridae. Proteins related to HCV have only been produced as recombinant constructs, and no complete HCV virion has been observed. The proteins are estimated to be translated at the following sizes: core 192 amino acids; possibly the 70 carboxy terminal of these is the matrix protein, which is based on the homology with members of the flaviviridae (Takamizawa, et al., ibid); the E1 192 amino acids, the E2-NS1 344 amino acids, the NS2 278 amino acids, the NS3 609 amino acids, the NS4 398 amino acids, and the NS5 998 amino acids.

The most variable regions of the HCV genome have been shown to reside within the probable envelope genes, whereas the 5' end and the core regions of the HCV genome seem to be highly conserved.

The main assays, so far, for studying the immunology of HCV has both in Europe and USA been the enzyme immuno assay (EIA) with the recombinant C-100 construct which covers parts of the NS4 protein (Kuo, et al., ibid). More recently assays containing either long synthetic peptides or recombinant peptides which cover both structural and non-structural HCV products, have been introduced (Hosein B, et al., Proc Natl Acad Sci USA 88:3647–51 (1991); Mimms L, et al., Lancet 336:1590–1 (1990)). The problems with the early, first generation, assays were both unsatisfactory sensitivity and specificity (Dawson G. J., et al., Journal of Clinical Microbiology 29:551–556 (1991)), though the second generation assays do seem to have improved the serology according to these problems (Chaudhary R. K., et al., J Clin Lab Anal 7:164–7 (1993); Chaudhary R. K., et al., Journal of Clinical Microbiology 29:2329–2330 (1991); Marcellin P, et al., Lancet 337:551–2 (1991)).

What is known about the immune response to HCV has mainly been obtained by using these assays. Most persons infected by HCV develop antibodies to one or more of the proteins, mainly the core and NS3/NS4 (Nasoff M. S., et al., Proc Natl Acad Sci USA 88:5462–6 (1991); Okamoto H, et al., Virology 188:331–341 (1992); Okamoto H, et al., Japanese Journal of Experimental Medicine 60:223–33 (1990); S̈allberg M, et al., Immunology Letters 33:27–34 (1992); S̈allberg M, et al., Journal of Clinical Microbiology 30:1989–1994 (1992)). Recombinant constructs covering these regions are termed c22 (core; Chiba J, et al., Proc Natl Acad Sci 88:4641–4645 (1991); Harada S, Journal of Virology 65:3015–21 (1991)), c33 (part of NS3), and C-100 (parts of NS3/NS4), and the C5-1-1 (a part of the C100-3 protein). The immune response to c22 and c33 have shortened the serodiagnosis of HCV in acute infections (Mattson L, et al., Scandinavian Journal of Gastroenterology 26:1257–1262 (1992)). No marker has been found to correlate to chronic infection, and IgM to different proteins have so far not been fully successful to be differentiating between acute and chronic infection. Only the persistant detection of HCV RNA by polymerase chain reaction (Garson J, et al., Lancet 335:1419–1422 (1990); Okamoto H, et al., Japanese Journal of Experimental Medicine 60:215–22 (1990); Weiner A. J., et al., Proceedings of the National Academy of Sciences USA 89:3468–3472 (1992)) has proven to be diagnostic for differentiating the acute from chronic carriers. One observation making HCV serology difficult is that seropositive individuals may loose their antibodies to HCV, or seronegative individuals may have HCV RNA. Immunity after HCV infection seems to be rather weak.

DESCRIPTION OF THE INVENTION

The present invention provides a new peptide of the formula

Met Ser Thr Asn Pro Lys Pro Cys Arg Lys Thr Lys Arg

Asn Thr Asn Arg Arg Pro Cys Asp Val Lys Phe Pro Gly

Gly Gly wherein there is a disulfide bridge between the two cysteine residues (SEQ ID NO: 1).

This synthetic peptide (HCV-15) has been chemically synthesized and the amino acid sequence thereof is similar to the N-terminal amino acids 1–28 of the amino acid sequence disclosed by Takeuchi, K et al., in Nucleic Acid Research 18:4626 (1990). However, the peptide of the invention, HCV-15, has two cysteine residues at positions 8 and 20, respectively, instead of Gln, and has further a disulphide bridge between said two cysteine residues formed by a chemical oxidation step.

The invention is further directed to a diagnostic antigen in carrier-bound form comprising the peptide according to the invention, HCV-15. The carrier may be coupled to the peptide by any suitable technique known in the art. The term "carrier" should be interpreted broadly, and it may be a surface, such as microtiter plate, glass or plastic beads, an amino acid residue, a peptide or a protein, such as keyhole limpet hemocyanine, bovine serum albumin, poly-L-lysine or a combination of such carriers as long as the carrier does not destroy the ability of the peptide of the invention to bind to HCV antibodies.

The diagnostic antigen of the invention does not only detect antibodies directed to HCV in a sample of body fluid, such as blood, salive or urine, but makes it also possible to differentiate between past and ongoing infection.

Thus, the invention is also directed to a method of in vitro diagnosing an active infection caused by hepatitis C virus which comprises subjecting a sample of body fluid from an individual to be diagnosed to an immunoassay making use of a diagnostic antigen according to the invention followed by evaluation of the level of reactivity obtained, low levels indicating past infection and high levels indicating active infection.

There are several known immunoassay techniques which can be used, such as radioimmunoassay (RIA), enzyme immunoassay (EIA), blot assays, such as Western blot, and agglutination assays, such as latex, particle and hemagglutinin. The detection methods are different in the different types of techniques, making use of certain types of markers as appropriate, but all immunoassay techniques are based on antibody-antigen reactivity, i.e. the amount of such complexes formed in relation to a standard or negative sample.

The diagnostic antigen according to the invention has been found to detect antibodies to the HCV core protein in more than 94% of persons with antibodies to the HCV (see Table 1). When compared to an anti-HCV core reactivity detected by a commercial assay containing a recombinant HCV core protein, the sensitivity of the HCV-15 EIA assay was found to be 89%–95% (see Tables 1 and 2).

When the method of in vitro diagnosing an active infection caused by hepatitis C virus of the invention was used, it was possible to discriminate between active and past infection by determination of the level of reactivity. When testing 134 samples, out of which 129 were reactive in different commercial anti-HCV EIAs, 84 were found to be positive for HCV RNA by PCR. Out of these 84 sera, 75 were reactive in the HCV-15 assay. The reactivity to the HCV-15 peptide of the invention was found to be significantly related to the presence of HCV RNA, as determined by PCR (p<0.01; see Table 3).

Further, the mean level of reactivity in the HCV-15 assay was found to be significantly higher in samples containing HCV RNA detected by the polymerase chain reaction (see Table 4). Thus, a high level of reactivity to the HCV-15 peptide is a sign of ongoing HCV infection.

Due to the high predictive value for the presence of HCV RNA when using the diagnostic antigen of the invention in an immunoassay, the method of diagnosing an active infection caused by HCV according to the invention may function as a rapid surrogate diagnosis for determining ongoing infection (see Tables 3 and 4).

It should be mentioned that the diagnostic antigen of the invention, which is a single cyclized synthetic peptide, has a specificity which is comparable to the presently available anti-HCV assays using multiple peptides or multiple recombinant antigens (see Tables 3–5).

Synthesis of the peptide of the Invention

The peptide of the invention is first synthesized in linear form making use of a suitable method commonly known in the art, such as genetic engineering, or coupling of one amino acid residue to the next or coupling of shorter sequenses in proper order, whereby peptide bonds are formed between residues, until the whole linear peptide is built-up, either in liquid medium or on a solid support (so-called solid phase synthesis). Then the linear peptide is subjected to a chemical oxidation step for ring-closure between the two cystein residues, whereby a disulfide bond is formed.

The solid phase technique was used for the synthesis of the peptide of the invention in accordance with the following references:

Merrifield, R. B. (1963) J. Am. Chem. Soc. 85:2149
Merrifield, R. B. (1964) Biochem. 3:1385
König, W. & Geiger, R. (1970) Chem. Ber. 103:788
Sheppard, R. C. (1973) In Nesvadba, H. (ed) Peptides 1971, North Holland, Amsterdam p. 111
Atherton, E., Gait, M. J., Sheppard, R. C. & Williams, B. J. (1979) Bioorg. Chem. 8:351
Sheppard, R. C. (1986) Science Tools 33:9–16
Atherton, E. & Sheppard, R. C. (1981) In Eberle, A., Geiger, R. & Wieland, T. (eds) Perspectives in Peptide Chemistry, Karger, Basel p. 101.

In addition to established three-letter codes for the amino acids, the following abbreviations are used:

| Boc | tert-butoxycarbonyl |
| DIPCDI | diisopropyl carbodiimide |
| DMF | dimethylformamide |
| EDT | ethanedithiol |
| FAB-MS | fast atom bombardment mass spectrometry |
| Fmoc | 9-fluorenylmethoxycarbonyl |
| HOBt | 1-hydroxybenzotriazole |
| OtBu | tert-butoxy |
| Pmc | pentamethylchromansulfonyl |
| POE | polyoxyethylene |
| tBu | tert-butyl |
| TFA | trifluoroacetic acid |
| Trt | triphenylmethyl |

All the amino acids used during the synthesis were protected by a Fmoc-group on the alpha-amino function. The following amino acids were protected in the side chain: Thr(tBu), Ser(tBu), Asn(Trt), Cys(Trt), Lys(Boc), Asp (OtBu) and Arg(Pmc).

The Amino acid derivatives were purchased from Cal-Biochem NovoBiochem GmbH, Badsoden, Germany.

The peptide of the invention having the formula SEQ ID NO: 1:

Met Ser Thr Asn Pro Lys Pro Cys Arg Lys Thr Lys Arg

Asn Thr Asn Arg Arg Pro Cys Asp Val Lys Phe Pro Gly

Gly Gly wherein there is a disulfide bridge between the two cysteine residues, was synthesized in accordance with the solid phase technique under continuous flow on a Milligen 9050 Peptide Synthesizer (Millipore Corp., Mass., USA) (Atherton, E., Sheppard, R. C. (1989) Solid Phase Synthesis A Practical Approach. Oxford, Oxford University Press.)

The resin used was of POE type with Rink-linker and a theoretical load of 0.23 meq/g (Rapp Polymer, Tubingen, Germany). The amino acids were activated with DIPCDI/HOBt in DMF and the N(alpha)-Fmoc group was removed by 20% piperidine in DMF. The product of the synthesis was dried in vacuum overnight. The peptide was then cleaved from the resin by treatment with TFA in the presence of EDT and phenol as scavengers (TFA:phenol:EDT 95:2.5:2.5). The TFA mixture and the peptide were precipitated by diethyl ether (100 ml) and filtrated. The precipitate was washed on the filter with additional diethyl ether (3×30 ml) and the cleaved-off peptide was extracted with water (100 ml). The extract was immediately diluted to a volume of 1 dm$^3$ with 20% acetic acid in methanol and was treated with a 0.1 mole/l solution of iodine in methanol until a faint yellow colour persisted.

Dowex 1×8 ion exchanger in acetate form (3 g) (Biorad, Richmond, Calif., USA) was then added, and the mixure was filtrated. The filtrate was subjected to evaporation and the residue was lyophilized from water.

The product was isolated by liquid chromatography (reversed phase). The stationary phase in the column consisted of Kromasil, 100 Å, $C_8$, 5 µ (EKA Nobel, Sweden; Hichrome Ltd, Reading, Berkshire, England), and the mobile phase was acetonitrile/water containing 0.1% of TFA. The samples collected from the coulmn were analyzed by an analytical HPLC (Varian 5500, Sunnyvale, Calif., USA) which was equipped with an analytical column having the same stationary phase as the above described one. Those fractions containing pure substance (HPLC analysis) were pooled and the solvent was evaporated. The product was lyophilized from water.

The final HPLC analysis was made on ready product. Purity (HPLC): 99.9%.

The structure was confirmed by FAB-MS. $[M+H]^+=3145$ (M-Scan Ltd, Sunninghill, Ascot, Berkshire, England), and by amino acid analysis (AAA) (Malmö Allmänna Sjukhus, Institutionen för Klinisk Kemi, Malmö, Sweden).

| AAA: AA | obtained | calculated |
|---|---|---|
| Asp,Asn | 3.93 | 4 |
| Arg | 3.95 | 4 |
| Cystine | 0.67 | 1 |
| Gly | 3.16 | 3 |
| Lys | 4.13 | 4 |
| Met | 0.99 | 1 |
| Phe | 1.01 | 1 |
| Pro | 3.89 | 4 |
| Thr,Ser | 3.84 | 4 |
| Val | 1.00 | 1 |

Detection of antibodies to HCV-15 by enzyme immunoassays (EIAs)

One-hundered µl of HCV-15 peptide was passively adsorbed overnight, at room temperature, to polystyrene microtiter plates (Nunc Maxisorb 96F Certificate, Nunc, Roskilde, Denmark) at a concentration of 10 µg peptide per mililiter of 0.05M sodium carbonate buffer, pH 9.6. Prior to addition of 100 µl human serum diluted 1:100 in phosphate buffered saline (PBS) containing 1% bovine serum albumin (BSA), 2% goat serum (Sigma Chemicals, St. Louis, Mo.), and 0.05% Tween 20 (dilution buffer), the plates were washed four times with PBS containing 0.05% Tween 20. The diluted human serum samples were incubated on the microtiter plate for 45 minutes at ±37° C. After additional washing to remove unbound material, 100 µl of alkaline phosphatase conjugated goat anti-human IgG diluted (A-3150, Sigma Chemicals) 1:1500 in dilution buffer, was added and incubated on the plate for 30 minutes at ±37° C. The plate was again washed to remove excess material, and 100 µl of dinitrophenylenediamine (1 mg/ml) was added to each well, followed by incubation on the plate for 30 minutes at room temperature (20°–22° C.). The enzyme reaction was then terminated by addition of 100 µl 1M NaOH to each well, and the absorbances were read at 405 nm using a double beam spectrophotometer. Absorbances exceeding the mean OD at 405 nm of at least 10 anti-HCV negative human sera by more than three times their standard devation were regarded as containing antibodies to the HCV-15 peptide.

TABLE 1

Relation between presence of antibodies to HCV in 2:nd generation Abbott EIA (Abbott, Chicago, Ill.) and presence of antibodies to HCV-15 in 88 Italian sera (kindly provided by Dr. Armando Gabrielli, Ancona)

| No. of sera reactive to HCV-15 | No. of sera reactive in Abbott anti-HCV EIA | | |
|---|---|---|---|
| | + | − | total |
| + | 70 | 0 | 70 |
| − | 4 | 14 | 18 |
| total | 74 | 14 | 88 | p < 0.01, Fisher's exact test.
Note: Sensitivity: 95%
Specificity: 100%

TABLE 2

Relation between antibody reactivity detected by the HCV-15 peptide EIA and Abbott Supplemental assay in 96 human sera provided by SBL, Stockholm.

| No. of sera reactive to HCV-15 | No. of sera reactive in Abbott Supplemental Assay | | | | |
|---|---|---|---|---|---|
| | Positive | Indeterminat | Negative | | |
| | S+/NS+ | S+/NS− | S−/NS+ | S/NS− | Total |
| + | 41 | 9 | 1 | 1 | 52 |
| − | 1 | 4 | 4 | 35 | 44 |
| Total | 42 | 13 | 5 | 36 | 96 |

Sensitivity 98% 69% 20% 97% (Specificity)

Abbreviations: S = bead coated with recombinant HCV core protein
NS = bead coated with recombinant HCV NS3 and NS4 proteins
Total sensitivity 85%

TABLE 3

Relation between the presence of HCV RNA and mean sample to cut-off ratio (S/CO) in HCV peptide EIAs of positive reactions using human sera.

| Peptide EIA | HCV RNA | No. sera positive in EIA | Mean S/CO ratio | SD | P-value (Whitney-Mann) |
|---|---|---|---|---|---|
| HCV-15 | + | 75 | 6,17 | 2,29 | 0,0352 |
| | − | 15 | 4,73 | 2,22 | |

Note: S/CO = the absorbance at 405 nm of the sample divided by the mean of the negative sera plus three times their standard deviation.

TABLE 4

Relation between presence of HCV RNA by PCR and antibodies to HCV-15 in 134 Swedish sera (kindly provided by Dr. Anders Sönnerborg, SMCL, Stockholm).

| HCV RNA | HCV-15 + | − | Total |
|---|---|---|---|
| + | 75 | 9 | 84 |
| − | 15 | 35 | 50 |
| Total | 90 | 44 | 134 |

$p < 0.01$, Fisher's exact test.
Note: Sensitivity: 89%
Specificity: 80%

TABLE 5

Relation between Abbott Supplemental and Organon 2 in 96 human sera obtained from SBL, Stockholm.

| No. of sera reactive in Organon 2 EIA | No. of sera reactive in Abbott Supplemental Assay | | | | |
|---|---|---|---|---|---|
| | Positive | | Indeterminat | Negative | |
| | S+/NS+ | S+/NS− | S−/NS+ | S−/NS− | Total |
| + | 41 | 7 | 4 | 0 | 52 |
| − | 1 | 6 | 1 | 36 | 44 |
| Total | 42 | 13 | 5 | 36 | 96 |

Sensitivity 98% 54% 80% 100% (Specificity)
Total sensitivity: 87%

TABLE 6

Relation between HCV-15 and Organon 2 in 96 human sera obtained from SBL, Stockholm.

| No. of sera reactive to HCV-15 | No. of sera reactive in Organon 2 anti-HCV EIA | | |
|---|---|---|---|
| | + | − | total |
| + | 48 | 4 | 52 |
| − | 4 | 40 | 44 |
| total | 52 | 44 | 96 |

Note: Sensitivity: 94%
Specificity: 91%

We claim:

1. A peptide of the formula

Met Ser Thr Asn Pro Lys Pro Cys Arg Lys Thr Lys Arg
Asn Thr Asn Arg Arg Pro Cys Asp Val Lys Phe Pro Gly
Gly Gly wherein there is a disulfide bridge between the two cysteine residues (SEQ ID NO: 1).

2. A diagnostic antigen in carrier-bound form comprising a peptide according to claim 1.

3. A method of in vitro diagnosing an active infection caused by hepatitis C virus which comprises
  subjecting a sample of body fluid from an individual to be diagnosed to an immunoassay making use of a diagnostic antigen according to claim 2
  followed by evaluation of the level of reactivity obtained, high levels indicating active infection.

* * * * *

UNITED STATES PATENT AND TRADEMARK OFFICE
CERTIFICATE OF CORRECTION

PATENT NO. : 5,716,779
DATED : February 10, 1998
INVENTOR(S) : Matti Sallberg et al.

It is certified that error appears in the above-identified patent and that said Letters Patent is hereby corrected as shown below:

Title page,
Item [73], Assignee, should read:
-- [73] Assignee: Euro-Diagnostica AB, Malmo, Sweden --

Signed and Sealed this

Twenty-second Day of February, 2005

JON W. DUDAS
*Director of the United States Patent and Trademark Office*